US008334892B2

(12) United States Patent
Takahashi (10) Patent No.: US 8,334,892 B2
(45) Date of Patent: Dec. 18, 2012

(54) IMAGE OBTAINMENT METHOD AND APPARATUS

(75) Inventor: Ryo Takahashi, Saitama (JP)

(73) Assignee: Fujifilm Corporation, Tokyo (JP)

( * ) Notice: Subject to any disclaimer, the term of this patent is extended or adjusted under 35 U.S.C. 154(b) by 666 days.

(21) Appl. No.: 12/457,937

(22) Filed: Jun. 25, 2009

(65) Prior Publication Data

US 2009/0322907 A1    Dec. 31, 2009

(30) Foreign Application Priority Data

Jun. 26, 2008    (JP) ................................ 2008-166707

(51) Int. Cl.
 *H04N 5/222* (2006.01)
(52) U.S. Cl. ........................................................ 348/42
(58) Field of Classification Search ..................... 348/42, 348/234; *H04N 5/222*
See application file for complete search history.

(56) References Cited

U.S. PATENT DOCUMENTS

| 5,032,913 | A  | * | 7/1991  | Hattori et al. ........... 348/70 |
| 2004/0207625 | A1 |   | 10/2004 | Griffin et al. |
| 2007/0153542 | A1 | * | 7/2007  | Gono et al. ........... 362/574 |
| 2007/0183162 | A1 |   | 8/2007  | Higuchi |
| 2008/0174701 | A1 | * | 7/2008  | Iketani et al. .......... 348/687 |

FOREIGN PATENT DOCUMENTS

| EP | 1 813 185 A1 | 8/2007 |
| JP | 2000-041942 A | 2/2000 |
| JP | 2003-93336 | 4/2003 |
| JP | 2003-126014 | 5/2003 |

OTHER PUBLICATIONS

European Search Report dated May 26, 2011.
Chinese Office Action dated Aug. 31, 2012 with partial English translation thereof.
Japanese Office Action dated Sep. 4, 2012 with partial English translation thereof.

* cited by examiner

*Primary Examiner* — Tung Vo
(74) *Attorney, Agent, or Firm* — McGinn IP Law Group, PLLC (57) ABSTRACT

An image obtainment apparatus images an observation target to obtain an ordinary image by illuminating the observation target with illumination light and by receiving, at an imaging device, reflection light reflected from the observation target. Further, the apparatus generates spectral estimation image signals of a predetermined wavelength by performing spectral image processing on image signals output from the imaging device. A spectral image processing unit generates spectral estimation image signals of a specific wavelength related to an agent administered to the observation target, as spectral estimation image signals for obtaining luminance information, based on the image signals output from the imaging device. Further, a luminance information obtainment unit obtains luminance information about each of the spectral estimation image signals for obtaining luminance information that have been generated at a predetermined time interval, and obtains a rate of change in the luminance information.

12 Claims, 5 Drawing Sheets

IMAGE OBTAINMENT METHOD AND APPARATUS

BACKGROUND OF THE INVENTION

1. Field of the Invention

The present invention relates to an image obtainment method and apparatus for imaging an observation target by administering an agent to the observation target. Particularly, the present invention relates to an image obtainment method and apparatus for imaging the observation target to observe a temporal change in the image of the observation target.

2. Description of the Related Art

Conventionally, endoscope apparatuses that can observe tissue in the body cavities of patients are well known. Further, electronic endoscopes that obtain ordinary-images of observation targets in the body cavities by imaging the observation targets illuminated with white light and display the ordinary-images on monitors are widely used in medical fields (for example, please refer to Japanese Unexamined Patent Publication No. 2003-126014).

In such endoscope apparatuses, for example, a dye such as ICG (indrocyanine green), which absorbs light of a specific wavelength, is sprayed onto or injected into tissue in vivo, which is an observation target. Further, in some cases, a change in the absorption characteristic is observed in time series to observe the properties of the tissue, such as the form and texture of the tissue. This method is often used to observe the flow of lymph to the sentinel lymph node of a patient.

However, the temporal change in the absorption characteristic, the fluorescence characteristic or the like of the observation target by administration of the aforementioned agent is minute. Therefore, it is very difficult to recognize the temporal change only by macroscopically observing an ordinary-image displayed based on image signals obtained by an imaging device. Consequently, the accuracy in diagnosis of the observation target becomes lower.

SUMMARY OF THE INVENTION

In view of the foregoing circumstances, it is an object of the present invention to provide an image obtainment method and apparatus that can obtain an image in such a manner that a temporal change in the absorption characteristic, the fluorescence characteristic or the like by administration of an agent to the observation target is more accurately recognized.

An image obtainment method of the present invention is an image obtainment method comprising the steps of:

imaging an observation target to obtain ordinary images of the observation target by illuminating the observation target with illumination light and by receiving, at an imaging device, reflection light reflected from the observation target; and generating spectral estimation image signals of a predetermined wavelength by performing spectral image processing on image signals output from the imaging device, wherein spectral estimation image signals of a specific wavelength related to an agent administered to the observation target are generated, as spectral estimation image signals for obtaining luminance information, based on the image signals output from the imaging device, and wherein luminance information about each of the spectral estimation image signals for obtaining luminance information that have been generated at a predetermined time interval is obtained and a rate of change in the luminance information is obtained.

An image obtainment apparatus of the present invention is an image obtainment apparatus comprising:

an illumination light illumination unit that illuminates an observation target with illumination light;

an imaging device that images the observation target to obtain an ordinary image of the observation target by receiving reflection light reflected from the observation target by illumination with the illumination light; and a spectral image processing unit that generates spectral estimation image signals of a predetermined wavelength by performing spectral image processing on image signals output from the imaging device, wherein the spectral image processing unit generates spectral estimation image signals of a specific wavelength related to an agent administered to the observation target, as spectral estimation image signals for obtaining luminance information, based on the image signals output from the imaging device, the apparatus further comprising:

a luminance information obtainment unit that obtains luminance information about each of the spectral estimation image signals for obtaining luminance information that have been generated at a predetermined time interval and obtains a rate of change in the luminance information.

Further, the image obtainment apparatus of the present invention may further include:

a color scheme setting unit that sets, based on the rate of change in the luminance information obtained by the luminance information obtainment unit, a color for each pixel of the image signals based on the ordinary images output from the imaging device or each pixel of the spectral estimation image signals generated by the spectral image processing unit; and a display unit that displays an ordinary-image based on the image signals after the color has been set by the color scheme setting unit or a spectral estimation image based on the spectral estimation image signals after the color has been set by the color scheme setting unit.

Further, the imaging device may be set in a scope unit that is inserted into the body cavity of a subject, and the spectral image processing unit may generate spectral estimation image signals of a specific wavelength that is different from the specific wavelength related to the agent administered to the observation target, as spectral estimation image signals for obtaining movement information, based on the image signals output from the imaging device. Further, the apparatus may further include:

a movement information obtainment unit that obtains, based on a difference between the spectral estimation image signals for obtaining movement information that have been generated at a predetermined time interval, movement information about an imaging range of the imaging device on the observation target; and a correction unit that corrects, based on the movement information obtained by the movement information obtainment unit, position information about the luminance information for each pixel of the spectral estimation image signals for obtaining luminance information.

Further, as the specific wavelength related to the agent, the absorption wavelength of the agent or the florescence wavelength of the agent may be used.

According to the image obtainment method and apparatus of the present invention, spectral estimation image signals of a specific wavelength related to an agent administered to the observation target are generated, as spectral estimation image signals for obtaining luminance information, based on the image signals output from the imaging device, and luminance information about each of the spectral estimation image signals for obtaining luminance information that have been generated at a predetermined time interval is obtained, and a rate of change in the luminance information is obtained. Therefore, for example, when colors are assigned, based on the rate of change in the luminance information, to image signals output from the imaging device and an image is displayed based on the image signals, it is possible to more accurately recognize a temporal change in the absorption characteristic and the fluorescence characteristic of the agent. Hence, the diagnosis accuracy (technique) improves. Further, when the temporal change is accurately recognized, it becomes possible to optimize the amount of the agent administered to the patient. Therefore, the present invention is beneficial to the QOL (quality of life) of the patient.

Further, in the image obtainment apparatus of the present invention, spectral estimation image signals of a specific wavelength that is different from the specific wavelength related to the agent administered to the observation target may be generated, as spectral estimation image signals for obtaining movement information, based on the image signals output from the imaging device, and movement information about an imaging range of the imaging device on the observation target may be obtained based on a difference between the spectral estimation image signals for obtaining movement information that have been generated at a predetermined time interval, and position information about the luminance information for each pixel of the spectral estimation image signals for obtaining luminance information may be corrected based on the obtained movement information. In that case, for example, when the image obtainment apparatus of the present invention is applied to an endoscope apparatus, even if the leading end of the scope unit swings or shakes, or the observation target, which is a living body, moves, and the imaging range moves, it is possible to correct the positional relationship among the pixels of each of the spectral estimation image signals for obtaining luminance information. Hence, it is possible to obtain the rate of change in the luminance information in an appropriate manner.

DESCRIPTION OF THE PREFERRED EMBODIMENTS

Figure 1:
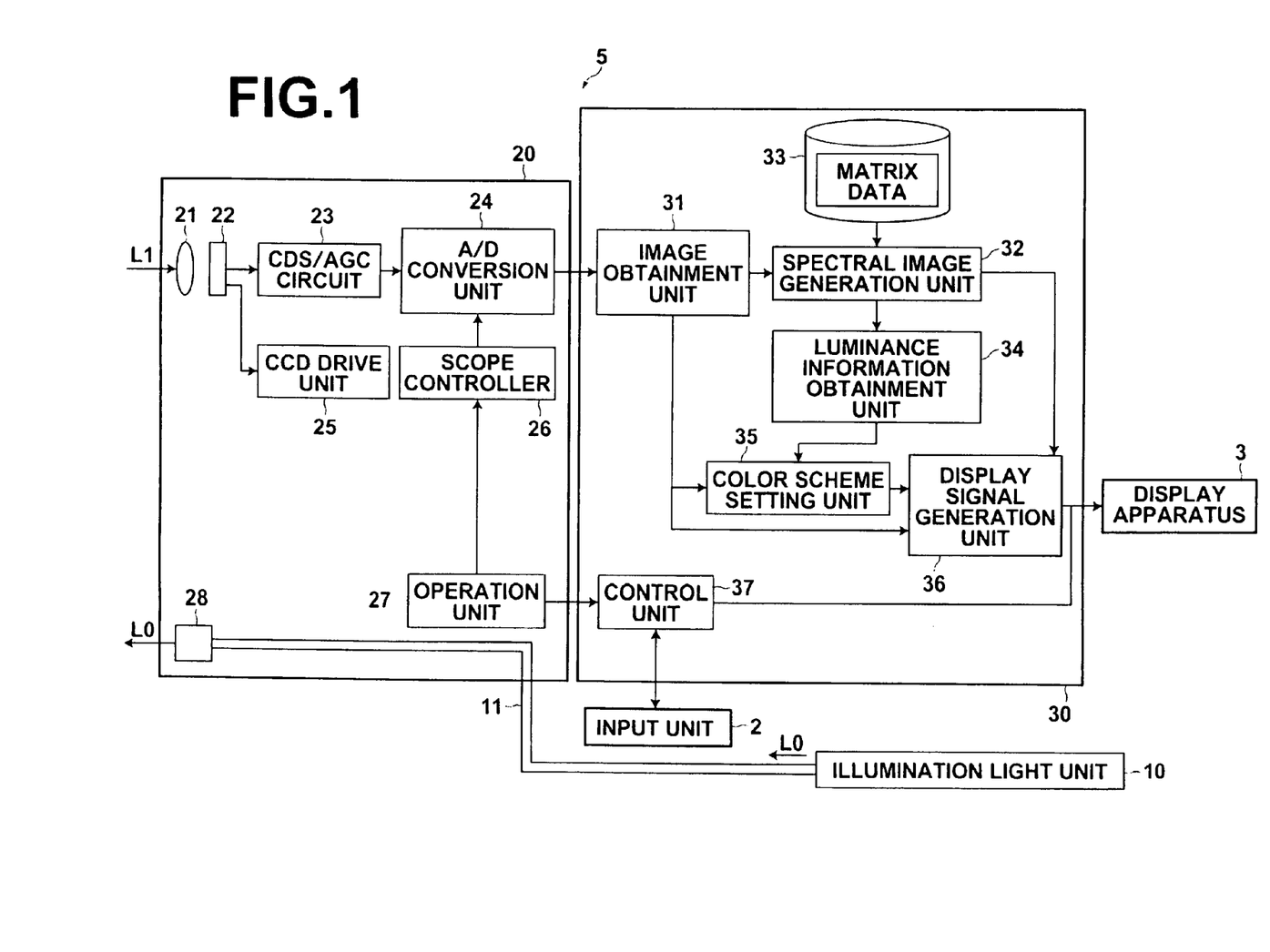
FIG. 1 is a schematic block diagram illustrating the configuration of an endoscope system using a first embodiment of an image obtainment apparatus of the present invention.

Hereinafter, an endoscope system using a first embodiment of an image obtainment apparatus according to the present invention will be described in detail with reference to the drawings. FIG. 1 is a schematic diagram illustrating the configuration of an endoscope system 1 using the first embodiment of the present invention.

As illustrated in FIG. 1, the endoscope system 1 includes a scope unit 20, a processor unit 30, and an illumination light unit 10. The scope unit 20 is inserted into the body cavity of a patient (a subject or person to be examined) to observe an observation target (an observation object or a region to be observed). The scope unit 20 is detachably connected to the processor unit 30. Further, the scope unit 20 is optically detachably connected to the illumination light unit 10. The illumination light unit 10 houses a xenon lamp that outputs illumination light L0. The processor unit 30 and the illumination light unit 10 may be structured as a unified body or as separate bodies.

The illumination light unit 10 outputs the illumination light L0 from the xenon lamp to perform ordinary observation. The illumination light unit 10 is optically connected to a light guide 11 of the scope unit 20, and the illumination light L0 enters the light guide 11 from an end of the light guide 11.

The scope unit 20 includes an image-formation optical system 21, an imaging device 22, a CDS/AGC (correlated double sampling/automatic gain control) circuit 23, an A/D (analog to digital) conversion unit 24, and a CCD (charge coupled device) drive unit 25, and each of the elements is controlled by a scope controller 26. The imaging device 22 is, for example, a CCD, a CMOS (complementary metal oxide semiconductor) or the like. The imaging device 22 performs photo-electric conversion on an image of the observation target, which has been formed on the imaging device 22 by the image-formation optical system 21, to obtain image information. As the imaging device 22, a complementary-color-type imaging device that has a color filter of Mg (magenta), Ye (yellow), Cy (cyan) and G (green) on the imaging surface thereof or a primary-color-type imaging device that has an RGB color filter on the imaging surface thereof may be used. In the description of the present embodiment, the primary-color-type imaging device is used. The operation of the imaging device 22 is controlled by the CCD drive unit 25. When the imaging device 22 obtains an image signal, the CDS/AGC (correlated double sampling/automatic gain control) circuit 23 performs sampling on the obtained image signal, and amplifies the sampled image signal. Further, the A/D conversion unit 24 performs A/D conversion on the image signal output from the CDS/AGC circuit 23, and outputs the image signal after A/D conversion to the processor unit 30.

Further, the scope unit 20 includes an operation unit 27 that is connected to the scope controller 26. The operation unit 27 can set various kinds of operations, such as switching of observation modes.

Further, an illumination window 28 is provided at the leading end of the scope unit 20, and the illumination window 28 faces an end of the light guide 11, the other end of which is connected to the illumination light unit 10.

The processor unit 30 includes an image obtainment unit 31, a spectral image generation unit 32, a storage unit 33, a luminance information obtainment unit 34, a color scheme setting unit 35, a display signal generation unit 36, and a control unit 37. The image obtainment unit 31 obtains a color image signal of three colors of R, G and B that has been generated based on an ordinary image obtained by the scope unit 20. The ordinary image is obtained (imaged) by the scope unit 20 by illuminating the observation target with the illumination light L0. The spectral image generation unit 32 performs spectral image processing on the color image signal obtained by the image obtainment unit 31 to generate a spectral estimation image signal of a predetermined wavelength. The storage unit 33 stores spectral estimation matrix data that are used to perform spectral image processing by the spectral image generation unit 32. The luminance information obtainment unit 34 obtains, at a predetermined time interval, spectral estimation image signals (spectral estimation image signals for obtaining luminance information) of a specific wavelength generated by the spectral image generation unit 32, and obtains a rate of change in luminance information about the spectral estimation image signals. The color scheme setting unit 35 sets the color scheme of each pixel of the color image signal obtained by the image obtainment unit 31 based on the rate of change in the luminance information about each of the pixels, which has been obtained by the luminance information obtainment unit 34. The display signal generation unit 36 generates an image signal for display by performing various kinds of processing on the color image signal after the color has been set (assigned) by the color scheme setting unit 35. The control unit 37 controls the whole processor unit 30. The operation of each of the elements will be described later in detail.

Further, an input unit 2 is connected to the processor unit 30. The input unit 2 receives an input by an operator. The input unit 2 can set an observation mode in a manner similar to the operation unit 27 of the scope unit 20. Further, the input unit 2 receives an input of operation, such as changing the wavelength of the spectral estimation image, changing the interval of imaging (photography) and the like, which will be described later.

A display apparatus 3 includes a liquid crystal display apparatus, a CRT (cathode-ray tube) or the like. The display apparatus 3 displays an ordinary-image, a spectral estimation image, or the like based on the image signal for display output from the processor unit 30. The action of the display apparatus 3 will be described later in detail.

Figure 2:
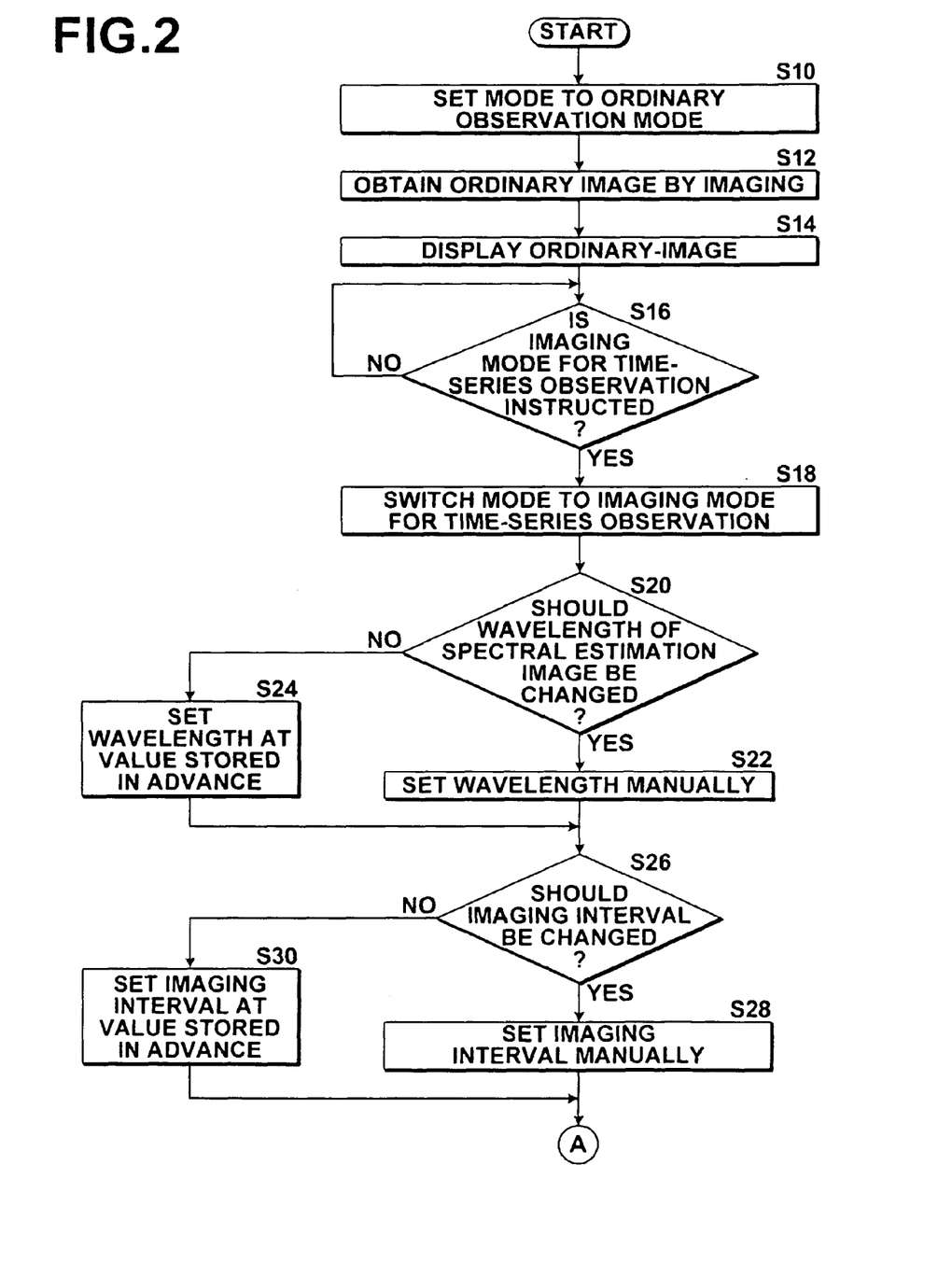
FIG. 2 is a flowchart for explaining the action of the endoscope system illustrated in FIG. 1.
Figure 3:
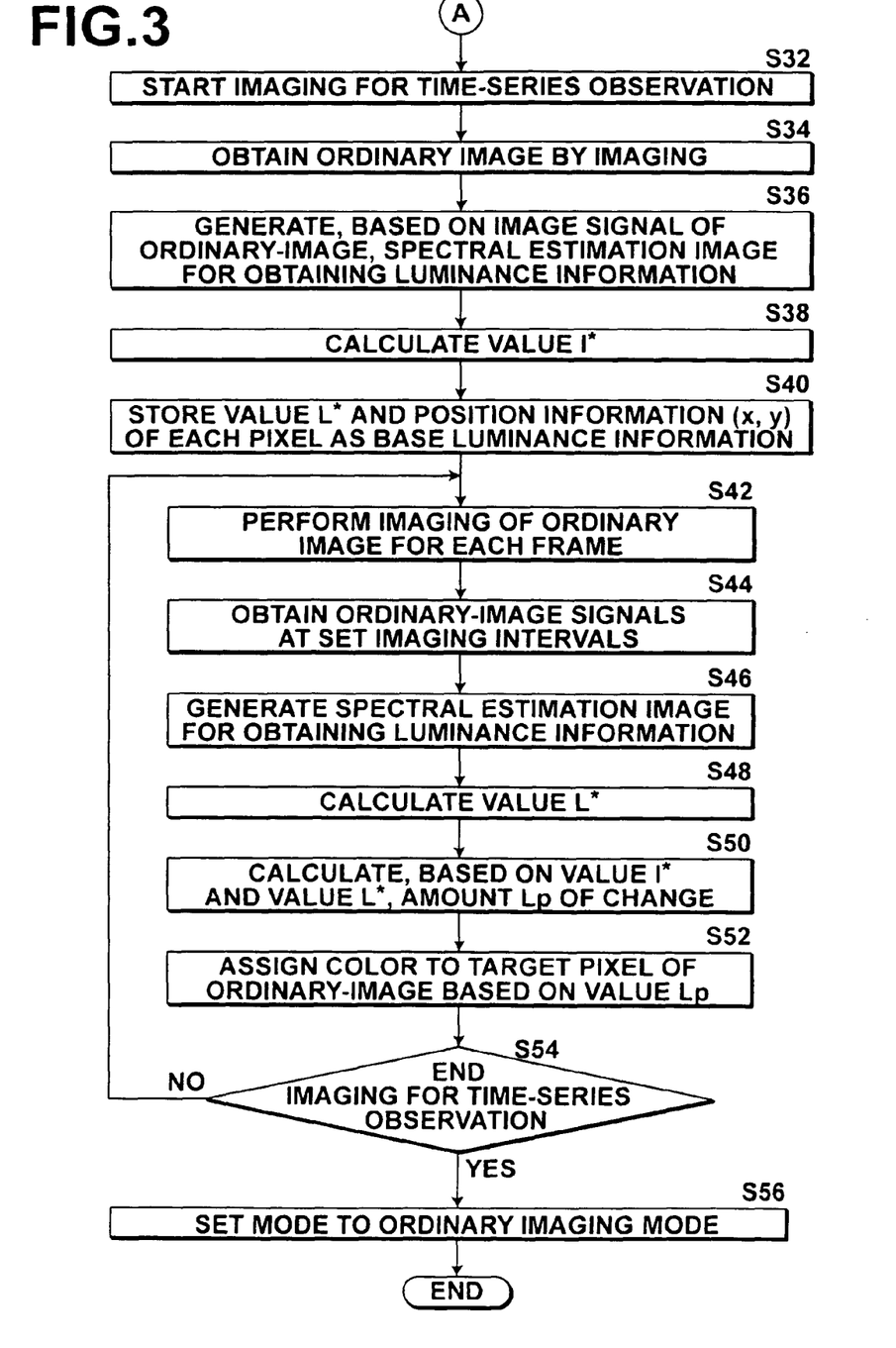
FIG. 3 is a flowchart for explaining the action of the endoscope system illustrated in FIG. 1.

Next, the operation of the endoscope system of the present embodiment will be described with reference to the flowcharts illustrated in FIGS. 2 and 3. First, an operation in an ordinary observation mode will be described. In the ordinary observation mode, an ordinary-image is displayed based on a color image signal obtained by illuminating the observation target with illumination light L0.

First, the ordinary observation mode is set (selected) by an operator at the operation unit 27 of the scope unit 20 or the input unit 2 (step S10). When the ordinary observation mode is set, the illumination light L0 is output from the illumination light unit 10. The illumination light L0 is transmitted through the light guide 11, and output through the illumination window 28 to illuminate the observation target. Further, reflection light L1 is reflected from the observation target that has been illuminated with the illumination light L0, and the reflection light L1 enters the image-formation optical system 21 of the scope unit 20. The image-formation optical system 21 forms an ordinary image on the imaging surface of the imaging device 22. Further, the imaging device 22 is driven by the CCD drive unit 25 to perform imaging on the ordinary image of the observation target. Accordingly, a color image signal representing the ordinary image is obtained (step S12). After the CDS/AGC circuit 23 performs correlated double sampling and amplification by automatic gain control processing on the color image signal, the A/D conversion unit 24 performs A/D conversion on the image signal on which the sampling and amplification have been performed to convert the analog signal to a digital signal. The digital signal is input to the processor unit 30.

The color image signal output from the scope unit 20 is obtained by the image obtainment unit 31 of the processor unit 30. The color image signal is output to the display signal generation unit 36. The display signal generation unit 36 performs various kinds of signal processing on the color image signal, and generates a Y/C signal composed of a luminance signal Y and chrominance signals C. Further, various kinds of signal processing, such as I/P conversion and noise removal, are performed on the Y/C signal to generate an image signal for display, and the image signal for display is output to the display apparatus 3. Further, the display apparatus 3 displays an ordinary-image based on the received image signal for display (step S14).

After the ordinary-image is displayed once as described above, the control unit 37 becomes a wait state, waiting for an instruction for an imaging mode for time-series observation (step S16). When the operator inputs an instruction for the imaging mode for time-series observation, the mode is switched to the imaging mode for time-series observation (step S18). When the mode is switched to the imaging mode for time-series observation, the control unit 37 makes the display apparatus 3 display a message asking whether the wavelength of the spectral estimation image signal for obtaining luminance information, which is used to calculate luminance information that will be described later, should be changed or not (step S20). When the operator looks at the message, he/she uses the input unit 2 to select whether the wavelength of the spectral estimation image signal for obtaining luminance information is set manually or automatically.

When the operator selects manual setting of the wavelength of the spectral estimation image signal for obtaining luminance information, a desirable wavelength is input, as the wavelength of the spectral estimation image signal for obtaining luminance information, at the input unit 2 by the operator. Further, the wavelength of the spectral estimation image signal for obtaining luminance information that has been received at the input unit 2 is output to the spectral image generation unit 32 (step S22).

In contrast, when the operator selects automatic setting of the wavelength of the spectral estimation image signal for obtaining luminance information, for example, the wavelength of the spectral estimation image signal for obtaining luminance information that has been stored in the control unit 37 in advance is read out. Further, the wavelength of the spectral estimation image signal for obtaining luminance information is output to the spectral image generation unit 32 (step S24).

Next, the control unit 37 makes the display apparatus 3 display a message asking whether the time interval of imaging for obtaining the spectral estimation image signals for obtaining luminance information, which are used to obtain luminance information that will be described later, should be changed (step S26). When the operator looks at the message, he/she uses the input unit 2 to select whether the time interval of imaging for obtaining the spectral estimation image signals for obtaining luminance information is set manually or automatically.

When the operator selects manual setting of the interval of imaging for obtaining the spectral estimation image signals for obtaining luminance information, a desirable interval is input, as the interval of imaging for obtaining the spectral estimation image signals for obtaining luminance information, at the input unit 2 by the operator. Further, the interval of imaging for obtaining the spectral estimation image signals for obtaining luminance information that has been received at the input unit 2 is output to the spectral image generation unit 32 (step S28).

In contrast, when the operator selects automatic setting of the interval of imaging for obtaining the spectral estimation image signals for obtaining luminance information, for example, the interval of imaging for obtaining the spectral estimation image signals for obtaining luminance information that has been stored in advance in the control unit 37 is read out. Further, the interval of imaging for obtaining the spectral estimation image signals for obtaining luminance information is output to the spectral image generation unit 32 (step S30).

After the wavelength and the interval of imaging of the spectral estimation image signals for obtaining luminance information are set as described above, imaging for time-series observation starts (step S32).

First, an ordinary image is obtained by imaging by illumination with the illumination light L0 in a manner similar to the operation in the aforementioned ordinary observation mode (step S34).

First, the color image signal obtained by the image obtainment unit 31 of the processor unit 30 is output to the spectral image generation unit 32. Further, the spectral image generation unit 32 generates a spectral estimation image signal for obtaining luminance information that has a predetermined wavelength. The predetermined wavelength is set in advance, as described above (step S36). Specifically, first, estimated reflection spectral data (q1 through q121) are calculated based on the received color image signal. The estimated reflection spectral data are calculated by performing a matrix operation represented by the following formula (1) on the color image signals R, G and B for each pixel. The matrix operation is performed by using a matrix of 3×121, including all parameters of spectral estimation matrix data, which is stored in the storage unit 33. Accordingly, estimated reflection spectral data (q1 though q121) are calculated.

$$\begin{bmatrix} q_1 \\ q_2 \\ \vdots \\ q_{121} \end{bmatrix} = \begin{bmatrix} k_{1r} & k_{1g} & k_{1b} \\ k_{2r} & k_{2g} & k_{2b} \\ \vdots & & \\ k_{121r} & k_{121g} & k_{121b} \end{bmatrix} \times \begin{bmatrix} R \\ G \\ B \end{bmatrix}$$ [Formula (1)]

Here, the spectral estimation matrix data are stored in advance, as a table, in the storage unit 33, as described above. Further, the spectral estimation matrix data are disclosed, in detail, in Japanese Unexamined Patent Publication No. 2003-093336, U.S. Patent Application Publication No. 20070183162, and the like. For example, in the present embodiment, the spectral estimation matrix data as shown in Table 1 are stored in the storage unit 33:

TABLE 1

| PARAMETER | $k_{pr}$ | $k_{pg}$ | $k_{pb}$ |
|---|---|---|---|
| p1 | $k_{1r}$ | $k_{1g}$ | $k_{1b}$ |
| . | . | . | . |
| . | . | . | . |
| . | . | . | . |
| p18 | $k_{18r}$ | $k_{18g}$ | $k_{18b}$ |
| p19 | $k_{19r}$ | $k_{19g}$ | $k_{19b}$ |
| p20 | $k_{20r}$ | $k_{20g}$ | $k_{20b}$ |
| p21 | $k_{21r}$ | $k_{21g}$ | $k_{21b}$ |
| p22 | $k_{22r}$ | $k_{22g}$ | $k_{22b}$ |
| p23 | $k_{23r}$ | $k_{23g}$ | $k_{23b}$ |
| . | . | . | . |
| . | . | . | . |
| . | . | . | . |
| p43 | $k_{43r}$ | $k_{43g}$ | $k_{43b}$ |
| p44 | $k_{44r}$ | $k_{44g}$ | $k_{44b}$ |
| p45 | $k_{45r}$ | $k_{45g}$ | $k_{45b}$ |
| p46 | $k_{46r}$ | $k_{46g}$ | $k_{46b}$ |
| p47 | $k_{47r}$ | $k_{47g}$ | $k_{47b}$ |
| p48 | $k_{48r}$ | $k_{48g}$ | $k_{48b}$ |
| p49 | $k_{49r}$ | $k_{49g}$ | $k_{49b}$ |
| p50 | $k_{50r}$ | $k_{50g}$ | $k_{50b}$ |
| p51 | $k_{51r}$ | $k_{51g}$ | $k_{51b}$ |
| p52 | $k_{52r}$ | $k_{52g}$ | $k_{52b}$ |
| . | . | . | . |
| . | . | . | . |
| . | . | . | . |
| p121 | $k_{121r}$ | $k_{121g}$ | $k_{121b}$ |

The spectral estimation matrix data in Table 1 include, for example, 121 wavelength band parameters (coefficient sets) p1 through p121, which are set by dividing the wavelength band of 400 nm to 1000 nm at intervals of 5 nm. Each of the parameters p1 through p121 includes coefficients $k_{pr}$, $k_{pg}$ and $k_{pb}$ (p=1 through 121) for matrix operations.

The spectral estimation image signals for obtaining luminance information of the predetermined wavelength are generated based on the estimated reflection spectral data (step S36). In the present embodiment, the spectral estimation image signals for obtaining luminance information that have the wavelength of 805 nm are generated. This wavelength is the maximum absorption wavelength of ICG (indocyanine green) agent or dye that will be administered to the observation target later. When the agent administered to the observation target is ICG, it is not necessary that the wavelength is 805 nm. The wavelength may be set at a predetermined wavelength in the range of from 780 nm through 805 nm (inclusive).

Specifically, estimated reflection spectral data q82 of the aforementioned wavelength are obtained, as an R component, a G component, and a B component of the spectral estimation image for obtaining luminance information, from the estimated reflection spectral data (q1 through q121).

The spectral estimation image signals for obtaining luminance information are output to the luminance information obtainment unit 34. Further, the luminance information obtainment unit 34 performs XYZ conversion on the R component, G component and B component of the spectral estimation image signal for obtaining luminance information of the wavelength of 805 nm. Further, value L* is calculated for each pixel based on a Y value obtained by the XYZ conversion (step S38).

The luminance information obtainment unit 34 uses the calculated value L* for each pixel as value l*, which is base luminance information, and stores the value l* in such a manner to correspond to the position information (x, y) of each pixel (step S40).

At this point of time, the agent is administered to the observation target. In the present embodiment, ICG is administered to the observation target.

After the agent is administered to the observation target, imaging of ordinary images is performed again at a predetermined frame rate in a manner similar to the operation in the aforementioned ordinary observation mode (step S42).

Color image signals obtained at the frame rate are sequentially output to the spectral image generation unit 32 and the color scheme setting unit 35.

The spectral image generation unit 32 obtains color image signals from the color image signals that are sequentially input to the spectral image generation unit 32. The spectral image generation unit 32 obtains the color image signals at timing of the interval of imaging that has been set in steps S28 through S30 (step S44). The interval of imaging is, for example, several tens of seconds and a few minutes.

Further, processing similar to step S36 is performed on the color image signal obtained in step S44 to generate the spectral estimation image signal for obtaining luminance information (step S46). Further, the spectral estimation image signal for obtaining luminance information is output to the luminance information obtainment unit 34. Further, value L* for each pixel is calculated in a manner similar to step S38 (step S48).

Next, the luminance information obtainment unit 34 reads out the value l*, which is base luminance information, that has been stored in advance in step S38. Further, the luminance information obtainment unit 34 calculates a rate Lp of change for each pixel based on this value l* and the value L* that has been calculated in step S48. The rate Lp of change is calculated by using the following formula (step S50):

$$Lp=\text{value } L^*/\text{value } l^*.$$

The rate Lp of change for each pixel that has been obtained by the luminance information obtainment unit 34 is output to the color scheme setting unit 35 together with the position information (x, y) of the respective pixels.

The color scheme setting unit 35 sets a color for each pixel of the color image signal output from the image obtainment unit 31. The color scheme setting unit 35 sets the color based on the value (magnitude) of the received rate Lp of change for each pixel to perform emphasis processing (step S52).

The color image signal after emphasis processing by the color scheme setting unit 35 is output to the display signal generation unit 36. The display signal generation unit 36 performs various kinds of image processing on the color image signal after emphasis processing, and generates a Y/C signal composed of a luminance signal Y and chrominance signals C. Further, various kinds of signal processing, such as I/P conversion and noise removal, are performed on the Y/C signal to generate an image signal for display. The image signal for display is output to the display apparatus 3. The display apparatus 3 displays, based on the received image signal for display, an ordinary-image after emphasis processing.

The processing in steps 42 through S52 is repeated until an instruction of ending imaging for time-series observation is input at the input unit 2 by the operator. Therefore, the ordinary-images after emphasis processing are sequentially updated and displayed (step S54).

Further, when the ordinary observation mode is set again by the operator at the operation unit 27 of the scope unit 20 or at the input unit 2, the operation returns to the aforementioned ordinary observation mode (step S56).

Figure 4:
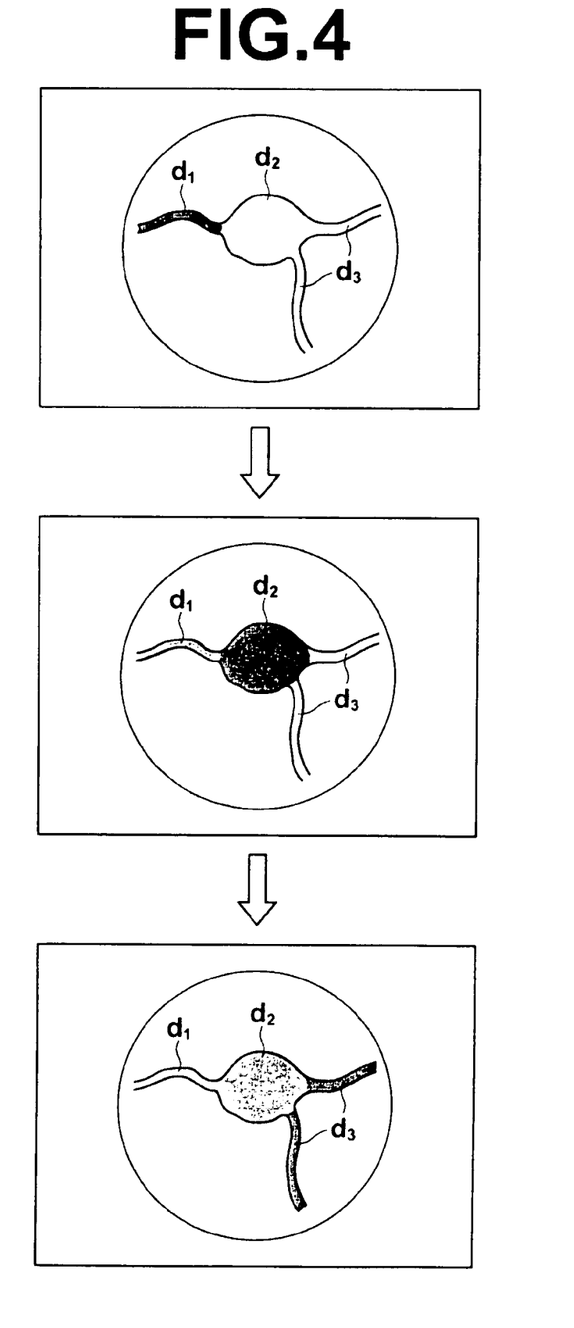
FIG. 4 is a schematic diagram illustrating a lymph node obtained by imaging in an imaging mode for time-series observation by the endoscope system illustrated in FIG. 1.

FIG. 4 is a schematic diagram illustrating images of a lymph node obtained by imaging the lymph node in imaging mode for time-series observation by using the endoscope system of the first embodiment of the present invention. In FIG. 4, the images were obtained in the order of from the top to the bottom. In each of the images illustrated in FIG. 4, lymph flows sequentially from portion $d_1$ to portion $d_2$, and further from portion $d_2$ to portion $d_3$.

In the image at the top of FIG. 4, ICG reached portion $d_1$, and the rate of change in luminance information in the portion $d_1$ increased. Therefore, the color of the portion $d_1$ is dark (deep, dense, intense or the like), as illustrated in FIG. 4. In the image at the center of FIG. 4, ICG reached portion $d_2$ from portion $d_1$, and the rate of change in luminance information in the $d_2$ portion increased. Therefore, the color of the portion $d_2$ is dark. At the same time, since the rate of change in luminance information in the portion $d_1$ is smaller than the rate of change in luminance information in the portion $d_2$, the color of the portion $d_1$ is lighter than that of the portion $d_2$, as illustrated in FIG. 4. Further, in the image at the bottom of FIG. 4, ICG reached portion $d_3$, and the rate of change in luminance information in the $d_3$ portion increased. Therefore, the color of the $d_3$ portion is dark. At the same time, since the rate of change in luminance information in the portion $d_2$ is smaller than the rate of change in luminance information in the portion $d_3$, the color of the portion $d_2$ is lighter than that of the portion $d_3$. Further, since the rate of change in luminance information in the portion $d_1$ is smaller than the rate of change in luminance information in the portion $d_2$, the color of the portion $d_1$ is even lighter than that of the portion $d_2$, as illustrated in FIG. 4.

In the endoscope system of the first embodiment, emphasis processing is performed on the ordinary-image based on the rate of change in luminance information. Alternatively, the endoscope system may be configured so that switching to an operation in spectral estimation image observation mode is possible. When the endoscope system is configured in such a manner, spectral estimation images of a predetermined wavelength may be generated in the spectral image generation unit 32, and emphasis processing may be performed on the spectral estimation images based on the rate of change in luminance information. Further, the images after emphasis processing may be displayed.

In the spectral estimation image observation mode, the steps from illumination of the illumination light L0 till obtainment of the color image signal are similar to the steps in the ordinary observation mode.

Further, the color image signal obtained by the image obtainment unit 31 is output to the spectral image generation unit 32.

In the spectral image generation unit 32, estimated reflection spectral data are calculated based on the received color image signal. The method for calculating the estimated reflection spectral data is similar to the aforementioned method for the imaging mode for time-series observation.

After the estimated reflection spectral data are calculated, for example, three wavelength bands λ1, λ2 and λ3 are selected by an operation at the input unit 2. Accordingly, estimated reflection spectral data corresponding to the selected wavelength bands are obtained.

For example, when wavelengths 500 nm, 620 nm and 650 nm are selected as the three wavelength bands λ1, λ2 and λ3, coefficients of parameters p21, p45 and p51 in Table 1, which correspond to these wavelengths, are used to calculate estimated reflection spectral data q21, q45 and q51.

Further, an appropriate gain and/or offset is applied to each of the obtained estimated reflection spectral data q21, q45 and q51 to calculate pseudo color spectral estimation data s21, s45 and s51. These pseudo color spectral estimation data s21, s45 and s51 are used as image signal R' of the R component of the spectral estimation image, image signal G' of the G component of the spectral estimation image, and image signal B' of the B component of the spectral estimation image, respectively. These spectral estimation image signals R', G' and B' are input to the color scheme setting unit 35.

The color scheme setting unit 35 performs emphasis processing by setting a color for each pixel of the spectral estimation image signal based on the value (magnitude) of the rate Lp of change for each pixel, which has been output from the luminance information obtainment unit 34.

Further, the spectral estimation image signal after emphasis processing at the color scheme setting unit 35 is output to the display signal generation unit 36. The display signal generation unit 36 performs various kinds of signal processing on the spectral estimation image signal after emphasis processing, and generates a Y/C signal composed of a luminance signal Y and chrominance signals C. Further, various kinds of signal processing, such as I/P conversion and noise removal, are performed on the Y/C signal to generate an image signal for display. The image signal for display is output to the display apparatus 3, and the display apparatus 3 displays, based on the received image signal for display, a spectral estimation image after emphasis processing.

In the above descriptions, the wavelengths 500 nm, 620 nm, and 650 nm were selected as the three wavelength bands λ1, λ2 and λ3. Such combinations of wavelength bands are stored in the storage unit 33. A combination of wavelength bands for each region to be observed, such as blood vessels and living body tissue for example, is stored. Therefore, a spectral estimation image of each region is generated by using a combination of wavelength bands that matches the region. Specifically, the sets of wavelengths λ1, λ2 and λ3 are, for example, eight combinations of wavelength bands, namely, standard set a, blood vessel B1 set b, blood vessel B2 set c, tissue E1 set d, tissue E2 set e, hemoglobin set f, blood—carotene set g, and blood—cytoplasm set h, or the like. The standard set a includes the wavelengths of 400 nm, 500 nm and 600 nm, and the blood vessel B1 set b includes the wavelengths of 470 nm, 500 nm, and 670 nm to extract blood vessels. The blood vessel B2 set c includes the wavelengths of 475 nm, 510 nm, and 685 nm to extract blood vessels. The tissue E1 set d includes the wavelengths of 440 nm, 480 nm, and 520 nm to extract a specific tissue. The tissue E2 set e includes the wavelengths of 480 nm, 510 nm, and 580 nm to extract a specific tissue. The hemoglobin set f includes the wavelengths of 400 nm, 430 nm, and 475 nm to extract a difference between oxyhemoglobin and deoxyhemoglobin. The blood—carotene set g includes the wavelengths of 415 nm, 450 nm, and 500 nm to extract a difference between blood and carotene. The blood—cytoplasm set h includes the wavelengths of 420 nm, 550 nm, and 600 nm to extract a difference between blood and cytoplasm.

In the endoscope system of the first embodiment of the present invention, since the absorption wavelength of the ICG agent administered to the observation target is in the range of from 780 nm through 805 nm (inclusive), the spectral estimation image signal of the wavelength of 805 nm was obtained as the spectral estimation image signal for obtaining luminance information. However, it is not necessary that the wavelength is 805 nm. A xenon lamp that is used as a light source for illumination light outputs white light, and the white light includes the wavelength of 700 nm, which is the wavelength of excitation light for ICG. When ICG is excited by the excitation light of the wavelength of 700 nm, ICG outputs fluorescence that has a peak in the vicinity of 830 nm. Therefore, spectral estimation image signal of the wavelength of 830 nm may be obtained as the spectral estimation image signal for obtaining luminance information.

Further, when a light source that does not include the wavelength band of excitation light is used as the light source for illumination light, a light source for excitation light should be separately provided.

Figure 5:
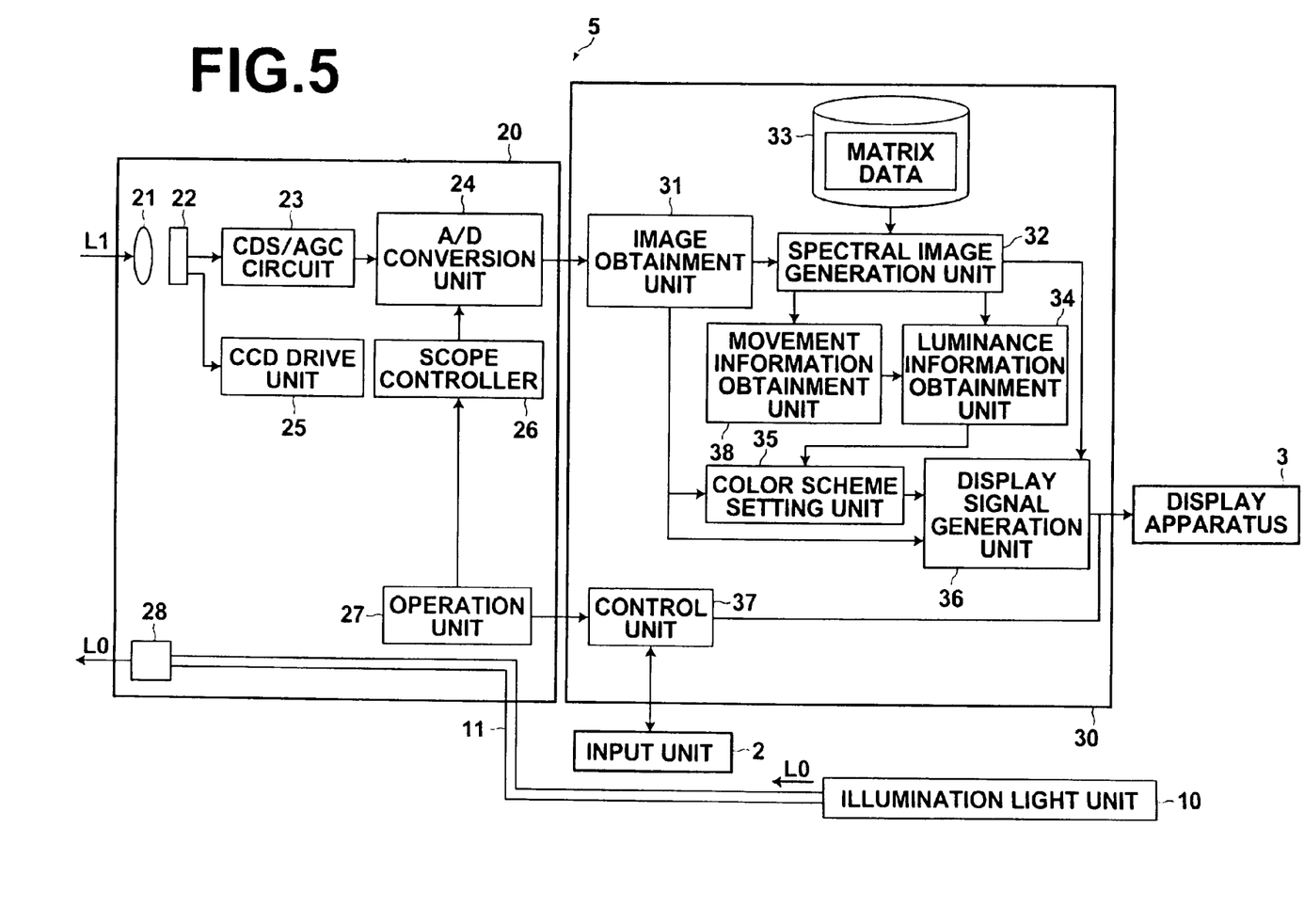
FIG. 5 is a schematic block diagram illustrating the configuration of an endoscope system using a second embodiment of an image obtainment apparatus of the present invention.

Next, an endoscope system using a second embodiment of the image obtainment apparatus of the present invention will be described in detail. FIG. 5 is a schematic diagram illustrating the configuration of an endoscope system 5 using the second embodiment of the present invention. In the endoscope system 5 using the second embodiment of the present invention, swings or shakes of the leading end of the scope unit 20 and the motion of the observation target in the imaging mode for time-series observation are further considered in addition to the functions of the endoscope system using the first embodiment of the present invention. Specifically, in the imaging mode for time-series observation, the observation target is imaged at predetermined intervals, and a temporal change in the observation target is observed. Therefore, the leading end of the scope unit 20 may swing or shake between imaging operations. Further, the observation target, which is a living body, may move during imaging. Therefore, the imaging range of the imaging device on the imaging target, in other words, the range of an imaging area on the imaging target that is imaged by the imaging device may move. If the imaging range on the imaging target changes between imaging before administration of an agent and imaging after administration of the agent, the ordinary image obtained by imaging when value l*, which is base luminance information, is obtained before administration of the agent and the ordinary image obtained by imaging when value L*, which is luminance information, is obtained after administration of the agent differ from each other. Consequently, it becomes impossible to calculate an accurate rate Lp of change in the luminance information for each pixel, and that results in erroneous display of images. Therefore, the endoscope system using the second embodiment of the present invention is configured so that such erroneous display can be prevented. Since other structures of the endoscope system using the second embodiment of the present invention are similar to the structures of the endoscope system using the first embodiment of the present invention, only elements different from the elements of endoscope system using the first embodiment of the present invention will be described.

As illustrated in FIG. 5, the endoscope system 5 includes a movement information obtainment unit 38. The movement information obtainment unit 38 calculates, based on spectral estimation image signal of a predetermined wavelength generated by the spectral image generation unit 32, the amount of movement in the imaging range of the scope unit 20. Further, the luminance information obtainment unit 34 has a correction unit. The correction unit corrects, based on the amount of movement calculated by the movement information obtainment unit 38, position information (x, y) about the value l*, which is the base luminance information.

Next, the operation of the endoscope system of the present embodiment will be described. Only the operations that are different from those of the endoscope system of the first embodiment will be described.

In the endoscope system of the second embodiment, when the spectral image generation unit 32 generates a spectral estimation image signal for obtaining luminance information to obtain value l*, which is the base luminance information, a spectral estimation image signal of a specific wavelength that is different from 805 nm is generated, as a spectral estimation image signal for obtaining movement information, in addition to the spectral estimation image signal of 805 nm for obtaining luminance information. As the specific wavelength that is different from 805 nm, a wavelength that is not related to the absorption wavelength nor the fluorescence wavelength of the agent administered to the observation target and that involves blood vessel information or a region that functions as an index for calculating the amount of movement is selected. When the agent is ICG, for example, a wavelength in the vicinity of 415 nm may be selected. When the wavelength is selected as described above, the spectral estimation image of the index area for calculating the amount of movement does not change between the image before administration of the agent and the image after administration of the agent. Therefore, the spectral estimation image of the index area can be used as a base for calculating the amount of movement. Further, the index area is not limited to the form of tissue, such as blood vessel information. For example, a marking applied to the observation target by cauterizing the observation target, which is a living body, a marking applied to the observation target by using dye or the like may be used as the index area.

Further, in the endoscope system of the second embodiment, when the spectral image generation unit 32 obtains value l*, which is base luminance information, the aforementioned spectral estimation image signal for obtaining movement information is also obtained. The obtained spectral estimation image signal for obtaining movement information is output to the movement information obtainment unit 38. Further, the movement information obtainment unit 38 determines, based on the received spectral estimation image signal for obtaining movement information, a plurality of index areas that function as base areas for calculating the amount of movement. The movement information obtainment unit 38 obtains, as base position information P0, position information about the index areas, and stores the obtained position information.

After the agent is administered, a spectral estimation image signal for obtaining luminance information is generated. When value L* is obtained, the spectral image generation unit 32 obtains spectral estimation image signal for obtaining movement information. The spectral estimation image signal for obtaining movement information is output to the movement information obtainment unit 38. The movement information obtainment unit 38 determines, based on the received spectral estimation image signal for obtaining movement information, a plurality of index areas as described above. Further, the movement information obtainment unit 38 obtains position information P1 for the index areas.

Further, the amount of movement between the imaging range when the value l*, which is the base luminance information, was obtained and the imaging range when the value L* was obtained is calculated based on base position information P0 obtained when the value l* was obtained and position information P1 when the value L* was obtained.

The amount of movement is output from the movement information obtainment unit 38 to the luminance information obtainment unit 34. The luminance information obtainment unit 34 corrects, based on the amount of movement, position information (x, y) for each pixel in the value l*, which is base luminance information that has been stored in advance. As a method for correcting the position information, for example, shift correction may be performed based on the amount of movement. Alternatively, deformation processing may be performed based on the amount of movement.

The luminance information obtainment unit 34 calculates the rate Lp of change in the luminance information for each pixel. The rate Lp of change is calculated based on value l*, which is base luminance information after correcting the position information (x, y) as described above, and the newly obtained value L*.

The rate Lp of change for each of the pixels obtained by the luminance information unit 34 is output to the color scheme setting unit 35.

Operations after this are similar to the operations in the endoscope system of the first embodiment.

In the endoscope systems according to the first embodiment and the second embodiment of the present invention, ICG was used as the agent. However, it is not necessary that ICG is used. Any agent may be used as long as the agent has a light absorption characteristic and a fluorescence characteristic at a specific wavelength. For example, AMCA (7-amino-4-methylcoumarin-3-acetic acid) or the like may be used.

Further, in the endoscope systems of the first embodiment and the second embodiment, the color of each pixel of an image signal representing an ordinary image or a spectral estimation image signal is set base on the rate of change in the luminance information. However, it is not necessary that the color is set in such a manner. For example, a luminance information image signal may be generated based on the rate of change in the luminance information, and a luminance information image based on the luminance information image signal may be superimposed on the ordinary-image or the spectral estimation image to display a synthesis image. Alternatively, the luminance information image may be displayed as an image separate from the ordinary-image and the spectral estimation image.

In the above descriptions, a case in which an embodiment of the image obtainment apparatus of the present invention is applied to an endoscope system was described. However, application of the image obtainment apparatus of the present invention is not limited to the endoscope system. The imaging obtainment apparatus of the present invention may be applied to a laparoscope, a colposcope or the like.

What is claimed is:

1. An image obtainment method, comprising:
   imaging an observation target to obtain ordinary images of the observation target by illuminating the observation target with illumination light and by receiving, at an imaging device, reflection light reflected from the observation target; and
   generating spectral estimation image signals of a predetermined wavelength by performing a spectral image processing on image signals output from the imaging device,
   wherein spectral estimation image signals of a specific wavelength related to an agent administered to the observation target are generated, as spectral estimation image signals for obtaining luminance information, based on the image signals output from the imaging device, the agent comprising a medical-chemical compound,
   wherein luminance information about each of the spectral estimation image signals for obtaining luminance information that have been generated at a predetermined time interval is obtained and a rate of change in the luminance information is obtained, and
   wherein the specific wavelength related to the agent comprises one of an absorption wavelength of the agent and a florescence wavelength of the agent.

2. An image obtainment apparatus, comprising:
   an illumination light illumination unit that illuminates an observation target with illumination light;
   an imaging device that images the observation target to obtain an ordinary image of the observation target by receiving reflection light reflected from the observation target by illumination with the illumination light;
   a spectral image processing unit that generates spectral estimation image signals of a predetermined wavelength by performing a spectral image processing on image signals output from the imaging device,
   wherein the spectral image processing unit generates spectral estimation image signals of a specific wavelength related to an agent administered to the observation target, as spectral estimation image signals for obtaining luminance information, based on the image signals output from the imaging device, the agent comprising a medical-chemical compound; and
   a luminance information obtainment unit that obtains luminance information about each of the spectral estimation image signals for obtaining luminance information that have been generated at a predetermined time interval and obtains a rate of change in the luminance information.

3. An image obtainment apparatus, as defined in claim 2, further comprising:
- a color scheme setting unit that sets, based on the rate of change in the luminance information obtained by the luminance information obtainment unit, a color for each pixel of the image signals based on the ordinary images output from the imaging device or each pixel of the spectral estimation image signals generated by the spectral image processing unit; and
- a display unit that displays an ordinary image based on the image signals after the color has been set by the color scheme setting unit or a spectral estimation image based on the spectral estimation image signals after the color has been set by the color scheme setting unit.

4. An image obtainment apparatus, as defined in claim 2, wherein the imaging device is set in a scope unit that is inserted into a body cavity of a subject, and
wherein the spectral image processing unit generates spectral estimation image signals of another specific wavelength that is different from the specific wavelength related to the agent administered to the observation target, as spectral estimation image signals for obtaining movement information, based on the image signals output from the imaging device, the apparatus further comprising:
- a movement information obtainment unit that obtains, based on a difference between the spectral estimation image signals for obtaining movement information that have been generated at a predetermined time interval, movement information about an imaging range of the imaging device on the observation target; and
- a correction unit that corrects, based on the movement information obtained by the movement information obtainment unit, position information about the luminance information for each pixel of the spectral estimation image signals for obtaining the luminance information.

5. An image obtainment apparatus, as defined in claim 3, wherein the imaging device is set in a scope unit that is inserted into a body cavity of a subject, and
wherein the spectral image processing unit generates spectral estimation image signals of another specific wavelength that is different from the specific wavelength related to the agent administered to the observation target, as spectral estimation image signals for obtaining movement information, based on the image signals output from the imaging device, the apparatus further comprising:
- a movement information obtainment unit that obtains, based on a difference between the spectral estimation image signals for obtaining movement information that have been generated at a predetermined time interval, movement information about an imaging range of the imaging device on the observation target; and
- a correction unit that corrects, based on the movement information obtained by the movement information obtainment unit, position information about the luminance information for each pixel of the spectral estimation image signals for obtaining the luminance information.

6. An image obtainment apparatus, as defined in claim 2, wherein the specific wavelength related to the agent comprises an absorption wavelength of the agent or a florescence wavelength of the agent.

7. An image obtainment apparatus, as defined in claim 2, wherein the spectral image processing unit generates the spectral estimation image signals for obtaining the luminance information by administering spectral image processes that employ spectral estimation matrix data on the image signals output from the imaging device.

8. An image obtainment apparatus, as defined in claim 7, wherein the spectral estimation matrix data includes wavelength band parameters, as coefficient sets, that are set at an interval.

9. An image obtainment apparatus, as defined in claim 2, wherein the spectral image processing unit generates the spectral estimation image signals for obtaining the luminance information based on estimated reflection spectral data that is calculated by performing a matrix operation on color image signals for each pixel.

10. An image obtainment apparatus, as defined in claim 9, wherein the spectral image processing unit performs the matrix operation by applying a matrix that includes spectral estimation matrix data stored in the spectral image processing unit.

11. An image obtainment apparatus, as defined in claim 10, wherein the spectral estimation matrix data includes wavelength band parameters, as coefficient sets, that are set at an interval.

12. An image obtainment method, as defined in claim 1, wherein the spectral estimation image signals for obtaining the luminance information are generated by administering spectral image processes that employ spectral estimation matrix data on the image signals output from the imaging device.

* * * * *